United States Patent [19]

Chibnik et al.

[11] 4,292,186

[45] Sep. 29, 1981

[54] METAL COMPLEXES OF ALKYLSUCCINIC COMPOUNDS AS LUBRICANT AND FUEL ADDITIVES

[75] Inventors: Sheldon Chibnik, Cherry Hill, N.J.; Ferdinand P. Otto, deceased, late of Sun City Center, Fla.; Helen F. Otto, executrix, Fort Lauderdale, Fla.

[73] Assignee: Mobil Oil Corporation, New York, N.Y.

[21] Appl. No.: 165,875

[22] Filed: Jul. 3, 1980

Related U.S. Application Data

[63] Continuation-in-part of Ser. No. 100,087, Dec. 4, 1979, abandoned, which is a continuation of Ser. No. 941,835, Sep. 11, 1978, abandoned, which is a continuation-in-part of Ser. No. 922,953, Jul. 10, 1978, abandoned, which is a continuation of Ser. No. 727,197, Sep. 27, 1976, abandoned.

[51] Int. Cl.$^3$ .......................... C10M 1/10; C10L 1/14
[52] U.S. Cl. ....................................... 252/49.7; 44/63; 44/68; 252/51.5 A; 252/56 D; 260/429 J; 260/429.3; 260/429.9; 260/438.1; 260/438.5 R; 260/439 R; 548/215; 548/237
[58] Field of Search .............. 252/49.7, 51.5 A, 56 D; 44/63, 68; 260/429.3, 429.9, 438.1, 438.5 R, 439 R, 429 J; 548/215, 237

[56] References Cited

U.S. PATENT DOCUMENTS

| | | | |
|---|---|---|---|
| 2,352,462 | 6/1944 | Weiss et al. | 252/49.7 X |
| 2,450,806 | 10/1948 | McCarthy | 252/49.7 X |
| 2,450,807 | 10/1948 | McCarthy | 252/49.7 X |
| 2,628,942 | 2/1953 | Morris et al. | 252/49.7 |
| 3,381,022 | 4/1968 | LeSuer | 252/56 D |
| 3,632,510 | 1/1972 | LeSuer | 252/49.7 X |
| 3,649,661 | 3/1972 | Otto et al. | 44/63 X |
| 3,697,428 | 10/1972 | Meinhardt et al. | 252/56 D |
| 3,755,167 | 8/1973 | Otto et al. | 44/68 X |
| 3,808,131 | 4/1974 | Otto et al. | 44/68 X |
| 3,945,933 | 3/1976 | Chibnik et al. | 44/63 X |
| 4,011,167 | 3/1977 | Chibnik et al. | 252/49.7 X |
| 4,017,406 | 4/1977 | Brois et al. | 252/51.5 A |
| 4,035,309 | 7/1977 | Brois | 252/51.5 A X |

*Primary Examiner*—Andrew Metz
*Attorney, Agent, or Firm*—Charles A. Huggett; Michael G. Gilman; Claude E. Setliff

[57] ABSTRACT

Fluid compositions containing a lubricant or liquid hydrocarbon fuel and a minor amount of a complex salt containing a 5- or 6-member ring are provided. These derivatives are made by complexing (1) the reaction product of an alcohol or an aminoalcohol with a succinic compound containing a long-chain hydrocarbon with (2) a metal salt. One such complex is one made by reacting a metal salt with the product of reaction between an alkylsuccinic acid or anhydride and said alcohol or aminoalcohol.

28 Claims, No Drawings

METAL COMPLEXES OF ALKYLSUCCINIC COMPOUNDS AS LUBRICANT AND FUEL ADDITIVES

CROSS-REFERENCE TO RELATED APPLICATIONS

This application is a continuation-in-part of U.S. Application Ser. No. 100,087, filed Dec. 4, 1979, now abandoned, which in turn is a continuation of U.S. Application Ser. No. 941,835, filed Sept. 11, 1978, now abandoned, which in turn is a continuation-in-part of U.S. Application Ser. No. 922,953, filed July 10, 1978, now abandoned, which in turn is a continuation of U.S. Application Ser. No. 727,197, filed Sept. 27, 1976, now abandoned.

BACKGROUND OF THE INVENTION

1. Field of the Invention

The invention is concerned with stabilized fuels and lubricants. More particularly, it relates to fuel and lubricant compositions to which have been added a complex formed from (1) the reaction product of an alkylsuccinic anhydride and a polyhydroxy compound and (2) a metal salt.

2. Discussion of the Prior Art

A great deal of effort has been directed to providing a lubricant which will permit present-day automotive engines to be operated at a high level of efficiency over long periods of time. A difficulty arises because lubricating oils tend to deteriorate under the conditions of use, with attendant formation of sludge, lacquer and resinous materials which adhere to the engine parts, thereby lowering the operating efficiency of the engine. To counteract the formation of these deposits, certain chemical additives have been found which, when added to lubricating oils, have the ability to keep the deposit-forming materials suspended in the oil, so that the engine is kept clean and in efficient operating condition for extended periods of time. These added agents are known in the art as detergents or dispersants.

Metallo-organic compounds are particularly useful as additives in this respect. However, the troublesome deposits which form on the skirt of the piston and on the walls of the combustion chamber, as well as on valves and spark plugs are also partially attributable to these metal-containing additives employed in the lubricant. Whenever oil is burned in the engine, as occurs with the oil film present on the cylinder wall during the combustion stroke, many metal-containing additives present in the oil may form an ash which is partially deposited on the various surfaces of the combustion chamber and on those of the spark plugs and valves.

Several known non-metallic detergents have previously been used in lubricating compounds. However, they have not proved to be entirely satisfactory. Additives which are particularly effective are based upon condensation of products of a hydroxyaromatic compound, an aldehyde and an amine, the so-called Mannich reaction. These additives are multi-functional improvers especially adapted for mineral oils and as pour point depressants therein. These compounds have also been recognized as exhibiting detergent properties. A preference has existed for the use of hydroxyaromatics which are unsubstituted, particularly phenol and alpha and beta naphthols.

U.S. Pat. No. 3,808,131 discloses a metal coordinated complex, useful as a detergent in lube oils and fuels, made by reacting an amine-acid product with an alkylsuccinic anhydride or acid and a metal salt. U.S. Pat. No. 3,755,167 describes a lube or fuel additive prepared by reacting an amine-aldehyde product with an alkylsuccinic acid or anhydride and a metal salt. This additive is also useful as a detergent. U.S. Pat. No. 3,632,510 discloses salt formation with materials similar to those used in the present invention.

SUMMARY OF THE INVENTION

The invention provides a metal complex product having 5 or 6 members in a ring prepared by first forming a non-acidic product of reaction between a polyalkenylsuccinic acid or anhydride and an amount sufficient to assure a non-acidic intermediate of a polyhydric alcohol or aminoalcohol of the formula

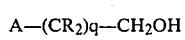

A—(CR$_2$)$_q$—CH$_2$OH wherein R is hydrogen, C$_1$–C$_{15}$ alkyl, hydroxyl, amino or CH$_2$OH, A is NH$_2$ or CH$_2$OH and q is 1 or 2, wherein at least on R group is hydroxyl, amino or CH$_2$OH, the remaining R groups being hydrogen, hydroxyl, C$_1$–C$_{15}$ alkyl, —CH$_2$OH or amino. It will be understood that when R is hydroxyl or amino only one such group will be attached to either carbon atom. In other words, neither individual carbon atom can contain more than one hydroxyl, one amino or a combination thereof. There is, however, no such restriction regarding the —CH$_2$OH group, so that both R groups (where q is 1) or all four R groups (where q is 2) can be —CH$_2$OH. Thus, the definition is meant to include those compounds wherein one or both carbon atoms can contain as one of the R groups one hydroxyl, one amino or one —CH$_2$OH, the other R groups being selected from hydrogen, C$_1$–C$_{15}$ alkyl or —CH$_2$OH. The reaction is carried out at from about 25° C. to about 275° C., and then reacting said product at from about 25° C. to about 200° C. with a metal salt, the metal being selected from Groups IB, IIB, IVB, VB, VIB, VIIB and VIII of the Periodic Table, the amount of salt used being at least equivalent to two of the OH or A functions or combinations thereof.

The invention also provides lubricant and fuel compositions comprising lubricant or fuel and a minor amount of the compounds just defined.

DESCRIPTION OF SPECIFIC EMBODIMENTS

The product produced may be an acid ester, or an imide, depending upon the reaction conditions and upon whether the hydroxy compound contains an amino group or not. For example, if one of the alcohols

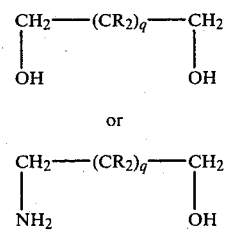

wherein q is 1 or 2 and R is as defined hereinabove is reacted with

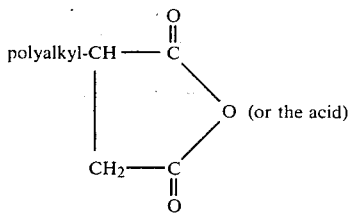

then there may be obtained a diester of the formula

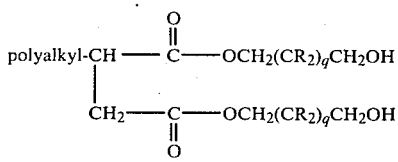

or an imide of the formula

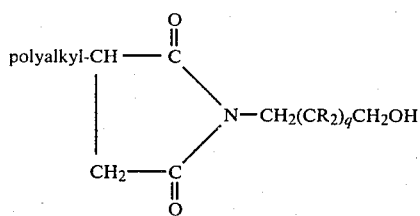

It will be understood that when the difunctional alcohol function is reacted with the polyalkylsuccinic compound, only one alcohol may react therewith, the other acid moiety being reacted with an alcohol function from another molecule. The important thing it that sufficient of the hydroxyl-containing compound be used so the intermediate will contain no appreciable acid functions. This will ordinarily be accomplished by using at least one mole proportion of the amino hydroxy compound and at least two mole proportions of the alcohol per mole proportion of succinic compound. "Mole proportion" includes fractional moles.

Also included are the oxazoline and the amide, made by reacting a nitrogen-containing alcohol and polyalkylsuccinic acid or anhydride. These may be exemplified by showing the use, for example, of 2-amino-2-methyl-1,3-propanediol to give the following type structures:

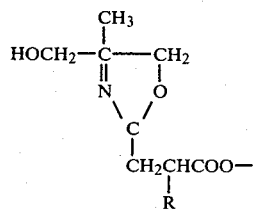   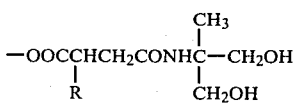

Oxazoline            Amide

Further, the invention includes products obtained, for example, from polyalkylamine, where the polyalkyl contains 50 to 300 carbon atoms, and an alkylene oxide. As an illustration, the reaction of polybutylamine with ethylene oxide yields a product having the structure
PB—NHCH$_2$CH$_2$OH, where PB is polybutyl.
It will be observed in all cases that, when the metal salt reacts with the above-noted compounds, the complex forms between the —OH groups or the —OH and —NH groups and contains a total of 5 or 6 members, including the metal salt. In the case of the oxazoline above, one obtains, on reacting with MX$_2$, where M is metal, a 5-membered ring as follows:

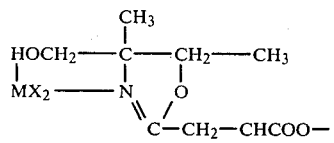

In general, the reaction between an alkylsuccinic acid or anhydride, such as polybutylsuccinic anhydride, with a polyhydroxy compound, as for example ethylene glycol, proceeds under relatively mild conditions. The preferred temperatures are from about 90° C. to about 200° C. Broadly, however, the temperatures can range from about 25° C. to about 275° C., depending upon the time of reaction and the size of the substituent as the polyhydroxy compound.

The preferred alkylsuccinic compound is one wherein the alkyl group, as has been stated, is a hydrocarbon containing from at least about 30 carbon atoms and more preferably from 50 to 300. These are produced by known techniques from an olefin or polyolefin and maleic anhydride. The olefin may be a simple alkene, such as 1-octene, 1-decene, 1-dodecene, and so forth, or it may be a polymer or copolymer of such olefins as ethene, propene, 1-butene, isobutene, 1-hexene, 1-octene and so forth.

As indicated hereinabove, the term "polyhydric alcohol" includes aliphatic polyhydric alcohols of the formula A—(CR$_2$)$_q$—CH$_2$OH wherein R, A and q are defined above. A is preferably —NH$_2$ or —OH. The aromatic nucleus can be a phenyl ring or a fused ring such as naphthalene or anthracene wherein the chelate-forming groups situated as follows:

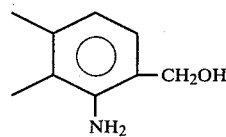

Illustrative of the nitrogen containing nuclei are 2-amino-2-methyl-1,3-propanediol and tris(hydroxymethyl) aminomethane.

The imides can be prepared by well known methods. U.S. Pat. No. 3,649,659, for example, teaches a reaction between an alkenylsuccinic acid or anhydride and an —NH-containing compound such as polyamine.

It should be readily apparent in all the above cases that chelate ring (as formed from two of the hydroxyls or from one hydroxyl and one amino) must have only 5 or 6 members therein, including the metal moiety. In preparing the complexes of the invention, the salts capable of forming such complexes include salts in which the metal is selected from the group consisting of metals from groups IB, IIB, IVB, VB, VIB, VIIB and VII of the Periodic Table.

Illustrative of the salts that may be employed are zinc acetate and propionate, cadmium formate and acetate, nickel formate and acetate and the like. They are preferably used in amounts equivalent to two of the hydroxyl functions or to 1 hydroxyl plus 1 amino function.

The temperature at which such salt is reacted will range from about 25° C. to about 200° C. for from about 5 minutes to 10 or more hours. The preferred temperature is from about 75° C. to about 125° C. for a time of 1 to about 4 hours.

When the compound $A-(CH_2)_qCH_2OH$ is reacted with polyalkylsuccinic acid or anhydride, the relative proportion of each is important only insofar as assuring that sufficient of it is used to assure a non-acidic produce for use in chelation. That is to say, such product must be free of acid functions. Otherwise, salt formation rather than chelation may occur or such salt formation may occur along with the chelation.

In all the reactions herein, a liquid medium may be used if desired. The medium may be one from which the product can be readily removed, as by distillation or filtration. Included are benzene, xylene and the like, as well as light petroleum oils suitable as solvents or suspending media.

Having described the invention in general terms, the following specific examples are offered as illustration.

EXAMPLE 1

One hundred seventy-five grams of polybutylsuccinic anhydride (PBSA) (from 1300 MW polybutene and maleic anhydride) was heated with 27 grams of pentaerythritol (PE) at 200° C. for 5 hours under a vacuum of 5 torr to remove the water reaction. The product was diluted with 164 g of mineral process oil and cooled. This material was treated with a solution of 22 g of zinc acetate dihydrate in 25 g of water for 1 hour at 90° C., the volatiles were removed by heating at 150° C. under vacuum for 1 hour and the product was diluted with 165 g of the process oil and filtered. The material contained 0.76% zinc.

EXAMPLE 2

In Example 1, a mole ratio of 1/2/1 (anhydride/polyol/zinc salt) was used. In this Example, there was used a mole ratio 1/1/1/ (238 g of PBSA+14 g of PE+22 g of $Zn(OAc)_2.2H_2O$+269 g of oil). A sample taken before the salt was added showed an acid value of only 3.8 (mg KOH/g) indicating that simple salt formation could not account for the 0.64% zinc found in the final product.

EXAMPLE 3

A material was prepared from a 1/1 mole ratio of polypropylsuccinic anhydride (from 850 MW polypropylene) and 2-amino-2-methyl-1,3-propanediol at 150° C. under vacuum for 3 hours. The product showed the presence of imide, ester, oxazoline and hydroxyl groups by infrared absorption, but no free amine was detected. Treatment of this material with an aqueous solution equivalent to 1 mole of zinc acetate as in the preceding Examples gave a product with 2.17% zinc.

EXAMPLE 4

Substitution of calcium acetate for the zinc acetate of Example 3 gave a material containing only 0.08% Ca. This shows that simple sale formation does not occur and that not all metals are suitable.

EXAMPLE 5

A solution of zinc methanesulfonate was prepared from 1.6 parts of zinc oxide, 5.6 parts of 70% methanesulfonic acid (aqueous solution) and 10 parts of water. The second component was prepared from one mole of tris(hydroxymethyl)aminomethane and one mole of PBSA as defined in Example 1 and diluted with one-half part of process oil. Using the procedure of the previous Examples, the salt solution was reacted with the second component and adjusted to a final product concentration of 55% in process oil. The material contained 0.78% zinc and 0.77% sulfur which indicates that all of the zinc methane sulfonate (normally insoluble in oil or organic media) had reacted.

EXAMPLES 6-12

The products of these Examples were prepared by the general method described in Example 3. The surfactant to be complexed (Example 6) was prepared from a 1/1 mole ratio of polybutyl (1300 number average MW) succinic anhydride and 2-amino-2-ethyl-1,3-propandiol. This was then treated with an equimolar amount of the salts in Examples 7-12.

Example 12 involves an alternate method of synthesis in that a complex of zinc acetate and aminoethylpropanediol was first formed by mixing aqueous solutions of the two compounds (1/1 mole ratio). Polybutylsuccinic anhydride (850 number average MW polybutylene) was added to the slurry which had formed and reacted at 150° C. for 3 hours under vacuum to remove water.

EVALUATION OF THE COMPOUNDS

The compounds of this invention were evaluated in the following tests:

Diesel Oil Test (DOT)

This test was developed to produce deposits from the oxidation of lubricating oil under conditions which closely approximate those found in the piston zone of a diesel engine. The test involves an aluminum cylinder heated by radiation from an external source. The surface temperature of the cylinder is maintained at 575° F. during the 140-minute test period. The shaft turns slowly (2 RPM) and dips into an oil sump where it picks up a thin film of oil. This thin film is carried into the oxidation zone where heated gases (moist air at 350° F. is typically employed, but nitrogen oxides, sulfur oxides and the like may be used) form oxidation deposits. These deposits can be affected by the detergent as the test cylinder rotates into the sump. The efficiency of the detergent is rated by the color and intensity of the deposits on the shaft at the end of the test.

Specifically, 20 parts of each complex (on a non-oil basis) was compounded with 947 parts of a solvent refined SAE 30 grade lubricating oil, 16 parts of calcium sulfonate, 4 parts of calcium phenate, 10 parts of zinc organodithiophosphate and 1 part of an acrylic ester polymer VI improver.

The results are shown in Table 1. In the test, 100 is clean.

TABLE 1

| Example | Salt Complexes | % Metal | DOT Rating |
|---------|----------------|---------|------------|
| Blank   | —              | —       | <50        |
| 1       | Zinc acetate   | 0.76    | 80         |
| 2       | Zinc acetate   | 0.64    | 84         |

TABLE 1-continued

| Example | Salt Complexes | % Metal | DOT Rating |
|---|---|---|---|
| 3 | Zinc acetate | 2.17 | 91 |
| 5 | Zinc methane sulfonate | 0.78 | 70 |
| 6 | None | — | 75 |
| 7 | Zirconylacetate | 0.16 | 70 |
| 8 | Copper (II) chloride | 1.18 | 71 |
| 9 | Cobalt (II) acetate | 0.25 | 78 |
| 10 | Chromium (III) nitrate | 0.24 | 69 |
| 11 | Zinc acetate | 1.53 | 78 |
| 12 | Zinc acetate | 2.8 | 80 |

Caterpillar 1-G Test

The conditions of the Caterpillar engine test were as follows:

An oil composition consisting of a blend of solvent refined mineral oils (SUV at 210° F. of 64.1) was used as the base fluid. This oil contained calcium sulfonate, calcium phenate, an acrylic ester polymer VI improver and zinc dithiophosphate.

The test engine was a single cylinder 4-cycle Caterpillar engine. It was run for three hours, the oil was changed and then subjected to a 480-hour endurance test under the following control parameters, with oil changes at 120 hour intervals.

| | |
|---|---|
| Speed, RPM | 1800 ± 10 RPM |
| Heat Input | 5850 ± 50 BTU/min. |
| Coolant Out Temp. °F. | 190 ± 5° F. |
| Oil to Brgs. Temp., °F. | 205 ± 5° F. |
| Inlet Air Temp., °F. | 255 ± 5° F. |
| Air P.S.I. to Engine | 53 ± in. Hg. Abs. |
| Oil P.S.I. at Jet Cooling Nozzle | 24 ± P.S.I. |

The piston was rated in accordance with the Coordinating Research Council rating system for diesel pistons. This system is a numerical demerit system wherein 8 categories of deposit are evaluated and deposit factors assigned. Location or multiplication factors are then assigned to 7 zones on the piston I.G. grooves, 1, 2, 3 and 4 and lands 2, 3 and 4. This location factor weighs the deposit heavier the lower it appears on the piston. These 7 weighted demerits are totaled for the W.T.D. (Weighted Total Demerit) rating. With the CRC Diesel Piston Rating System, 0=clean and the maximum 1G piston demerit=17,450. The material of Example 3, compounded the same as the materials of Table 1, was tested and rated, under the CRC Diesel Rating System, which includes the weighted total deposits (WTD) and top groove packing (TGP). The test oil had a WTD of 118.7 and 75% top groove packing. A comparative test with a commercial polyester detergent (comparable to the component which was complexed in Example 1) gave a rating of 152.3 WTD and 88% TGP.

The additives of this invention can be used in any one of a wide variety of oils of lubricating viscosity, such as natural, refined or synthetic oils, in blends of such oils, or in greases made therefrom. These oils may be prepared with or without auxiliary conventional additives such as: oiliness and extreme pressure agents; corrosion, oxidation and rust inhibitors; viscosity index improving agents; coloring agents; and auxiliary detergents. The useful oils include mineral oils, both naphthenic and paraffinic, either or both containing aromatic fractions. They include, among the synthetic oils, the synthetic hydrocarbon oils as well as synthetic ester oils prepared from, for example, monohydric alcohols and polyfunctional acids or from the polyhydric alcohols and monofunctional acids. In this latter category are esters prepared from pentaerythritol and a $C_5$ aliphatic mono acid such as valeric acid of from such alcohol and a mixture of $C_5$–$C_9$ aliphtic monofunctional acids.

The fuels contemplated are liquid hydrocarbon combustion fuels, including the distillate fuels, i.e. gasoline and fuel oils. Accordingly, the fuel oils that may be improved in accordance with the present invention are hydrocarbon fractions having an initial boiling point of at least about 100° F. and an end-boiling point no higher than about 750° F. and boiling substantially continuously throughout their distillation range. These fuel oils are generally known as distillate fuel oils. It is to be understood, however, that this term is not restricted to straight run distillate fractions. The distillate fuel oils can be straight run distillate fuel oils, catalytically or thermally cracked (including hydrocracked) distillate fuel oils, or mixture of straight run distillate fuel oils, naphthas and the like, with cracked distillate stocks. Moreover, such fuel oils can be treated in accordance with well-known commercial methods, including acid or caustic treatment, hydrogenation, solvent refining, clay treatment and the like.

The distillate fuel oils are characterized by their relatively low viscosities, pour points, and similar properties. The principal property which characterizes the contemplated hydrocarbons, however, is the distillation range. As mentioned hereinbefore, this range lies between about 100° F. and about 750° F. Obviously, the distillation range of each individual fuel oil will cover a narrower boiling range, but falling, nevertheless, within the above-specified limits. Likewise, each fuel oil will boil substantially continuously throughout its distillation range.

Contemplated among the fuel oils are Nos. 1, 2 and 3 fuel oils (useful in heating and in diesel engines) and the jet combustion fuels. The domestic fuel oils generally conform to the specifications set forth in A.S.T.M. Specification D396-48T. Specifications for diesel fuels are defined in A.S.T.M. specification D975-48T. Typical jet fuels are defined in Military Specification MIL-F-5624B.

The gasolines that are improved by the additive compositions of this invention are mixtures of hydrocarbons having an initial boiling point falling between about 75° F. and about 135° F. and an end-boiling point falling between about 250° F. and about 450° F. As is well known in the art, motor gasoline can be straight run gasoline or, as is more usual, it can be a blend of two or more cuts of materials including straight run stock, catalytic or thermal reformate, cracked stock alkylated natural gasoline and aromatic hydrocarbons. All of these are contemplated.

We claim:

1. A metal complex prepared by (1) forming a nonacidic product of reaction between 1 mole proportion of a polyalkenylsuccinic acid or anhydride and from about 1 to about 2 mole proportions of a polyhydric alcohol or aminoalcohol of the formula

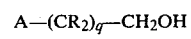

$$A-(CR_2)_q-CH_2OH$$

wherein R is hydrogen, a $C_1$–$C_{15}$ alkyl, hydroxyl, amino or —$CH_2OH$, A is $NH_2$ or —$CH_2OH$ and q is 1 to 2, wherein at least one R group is hydroxyl, amino or —$CH_2OH$, the remaining R groups being hydrogen, hydroxyl, $C_1$–$C_{15}$ alkyl, —$CH_2OH$ or amino, the reaction being carried out at from about 25° C. to about 275° C., and (2) reacting said product at from about 25° C. to about 200° C. with a metal salt, the metal being selected from Groups IB, IIB, IVB, VB, VIB and VIII of the Periodic Table, the amount of salt used being at least equivalent to two of the —OH or —A functions or combinations thereof.

2. The product of claim 1 wherein the alkenyl is a hydrocarbon containing from 50 to about 300 carbon atoms.

3. The product of claim 1 wherein the metal is zinc.

4. The product of claim 1 wherein the metal is zirconium.

5. The product of claim 1 wherein the metal is copper.

6. The product of claim 1 wherein the metal is cobalt.

7. The product of claim 1 wherein the metal is chromium.

8. The product of claim 1 wherein the alkenyl group has a molecular weight of 1300.

9. The product of claim 1 wherein the alkenyl group has a molecular weight of 850.

10. The product of claim 1 wherein the said non-acidic product is prepared from polybutylsuccinic anhydride and pentaerythritol.

11. The product of claim 1 wherein the said non-acidic product is prepared from polypropylsuccinic anhydride and 2-amino-2-methyl-1,3-propanediol.

12. The product of claim 1 wherein the said non-acidic product is prepared from polybutylsuccinic anhydride and tris(hydroxymethyl)aminomethane.

13. The product of claim 1 wherein the said non-acidic product is prepared from polybutylsuccinic anhydride and 2-amino-2-ethyl-1,3-propanediol.

14. A lubricant or fuel composition comprising a major proportion of a lubricating oil, a grease thereof or a liquid hydrocarbon fuel and a detergent amount of a metal complex as defined in claim 1.

15. The composition of claim 14 wherein the alkenyl is a hydrocarbon containing from 50 to about 300 carbon atoms.

16. The composition of claim 14 wherein the metal is zinc.

17. The composition of claim 14 wherein the metal is zirconium.

18. The composition of claim 14 wherein the metal is copper.

19. The composition of claim 14 wherein the metal is cobalt.

20. The composition of claim 14 wherein the metal is chromium.

21. The composition of claim 14 wherein the alkenyl has a molecular weight of 1300.

22. The composition of claim 14 wherein the alkenyl has a molecular weight of 850.

23. The composition of claim 14 wherein the said non-acidic product is prepared from polybutylsuccinic anhydride and pentaerythritol.

24. The composition of claim 14 wherein the said non-acidic product is prepared from polypropylsuccinic anhydride and 2-amino-2-methyl-1,3-propanediol.

25. The composition of claim 14 wherein the said non-acidic product is prepared from polybutylsuccinic anhydride and tris(hydroxymethyl)aminomethane.

26. The composition of claim 14 wherein the said non-acidic product is prepared from polybutylsuccinic anhydride and 2-amino-2-ethyl-1,3-propanediol.

27. The product of claim 11 wherein the mole ratio of acid or anhydride to alcohol or amino alcohol is 1:2.

28. The composition of claim 14 wherein the mole ratio of acid or anhydride to alcohol or amino alcohol is 1:2.

* * * * *